(12) United States Patent
Ouchi et al.

(10) Patent No.: US 7,351,201 B2
(45) Date of Patent: Apr. 1, 2008

(54) TREATMENT INSTRUMENT FOR ENDOSCOPE

(75) Inventors: Teruo Ouchi, Saitama (JP); Makoto Kobayashi, #10C 3-18, Unomori 2-chome, Yokkaichi-shi, Mie (JP)

(73) Assignees: PENTAX Corporation, Tokyo (JP); Makoto Kobayashi, Yokkaichi-shi (JP)

( * ) Notice: Subject to any disclaimer, the term of this patent is extended or adjusted under 35 U.S.C. 154(b) by 406 days.

(21) Appl. No.: 11/014,032

(22) Filed: Dec. 17, 2004

(65) Prior Publication Data

US 2005/0137453 A1 Jun. 23, 2005

(30) Foreign Application Priority Data

Dec. 19, 2003 (JP) .......................... P2003-421742
Feb. 10, 2004 (JP) .......................... P2004-032896

(51) Int. Cl.
*A61B 1/00* (2006.01)

(52) U.S. Cl. .................. 600/104; 600/127; 600/129

(58) Field of Classification Search ................ 600/104, 600/127, 129; 606/46, 47
See application file for complete search history.

(56) References Cited

U.S. PATENT DOCUMENTS

| | | |
|---|---|---|
| 5,133,727 A | 7/1992 | Bales et al. |
| 5,133,735 A | 7/1992 | Slater et al. |
| 5,133,736 A | 7/1992 | Bales, Jr. et al. |
| 5,141,519 A | 8/1992 | Smith et al. |
| 5,152,778 A | 10/1992 | Bales, Jr. et al. |
| 5,156,633 A | 10/1992 | Smith |
| 5,170,800 A | 12/1992 | Smith et al. |
| 5,171,256 A | 12/1992 | Smith et al. |
| 5,171,258 A | 12/1992 | Bales et al. |
| 5,174,300 A | 12/1992 | Bales et al. |
| 5,176,702 A | 1/1993 | Bales et al. |
| 5,192,298 A | 3/1993 | Smith et al. |
| 5,203,785 A | 4/1993 | Slater |
| 5,215,101 A | 6/1993 | Jacobs et al. |
| 5,228,451 A | 7/1993 | Bales et al. |
| 5,234,453 A | 8/1993 | Smith et al. |
| 5,241,968 A | 9/1993 | Slater |

(Continued)

FOREIGN PATENT DOCUMENTS

JP          3-295551          12/1991

(Continued)

OTHER PUBLICATIONS

English language abstract of JP 3-295551.

(Continued)

*Primary Examiner*—John P. Leubecker
*Assistant Examiner*—Victoria W Chen
(74) *Attorney, Agent, or Firm*—Greenblum & Bernstein, P.L.C.

(57) ABSTRACT

A treatment instrument for an endoscope includes: a front end hood that is provided to a distal end of an inserting portion of the endoscope; a supporting member that is provided inside the front end hood; a treatment member that is rotatably supported by the supporting member; and an operating wire that is coupled to the treatment member and extended rearwardly from the front end hood. The treatment member is rotated about the supporting member by operating to extract and retract the operating wire at a base side of the endoscope.

18 Claims, 18 Drawing Sheets

U.S. PATENT DOCUMENTS

| | | |
|---|---|---|
| 5,258,004 A | 11/1993 | Bales et al. |
| 5,269,804 A | 12/1993 | Bales et al. |
| 5,275,612 A | 1/1994 | Bales et al. |
| 5,293,878 A | 3/1994 | Bales et al. |
| 5,320,636 A | 6/1994 | Slater |
| 5,331,971 A | 7/1994 | Bales et al. |
| 5,392,789 A | 2/1995 | Slater et al. |
| 5,395,386 A | 3/1995 | Slater |
| 5,396,900 A | 3/1995 | Slater et al. |
| 5,431,645 A | 7/1995 | Smith et al. |
| 5,439,478 A | 8/1995 | Palmer |
| 5,443,480 A | 8/1995 | Jacobs et al. |
| 5,482,054 A | 1/1996 | Slater et al. |
| 5,507,296 A | 4/1996 | Bales et al. |
| 5,507,297 A | 4/1996 | Slater et al. |
| 5,531,755 A | 7/1996 | Smith et al. |
| 5,613,499 A | 3/1997 | Palmer et al. |
| 5,666,965 A | 9/1997 | Bales et al. |
| 6,033,424 A | 3/2000 | Ouchi |
| 6,041,679 A | 3/2000 | Slater et al. |
| 6,080,102 A * | 6/2000 | Konou et al. ............... 600/114 |
| 6,110,127 A * | 8/2000 | Suzuki ...................... 600/565 |
| 6,206,904 B1 | 3/2001 | Ouchi |
| 6,264,617 B1 | 7/2001 | Bales et al. |
| 6,551,315 B2 * | 4/2003 | Kortenbach et al. .......... 606/46 |
| 6,605,104 B2 | 8/2003 | Sato et al. |
| 6,719,763 B2 * | 4/2004 | Chung et al. ............... 606/144 |
| 7,087,010 B2 * | 8/2006 | Ootawara et al. ........... 600/104 |
| 2004/0059253 A1 | 3/2004 | Martone et al. |

FOREIGN PATENT DOCUMENTS

| | | |
|---|---|---|
| JP | 63-151111 | 12/1991 |
| JP | 5-9503 | 2/1993 |
| JP | 7-8450 | 1/1995 |
| JP | 9-66019 | 3/1997 |
| WO | 03/057044 | 7/2003 |

OTHER PUBLICATIONS

English language abstract of JP7-8450.

* cited by examiner

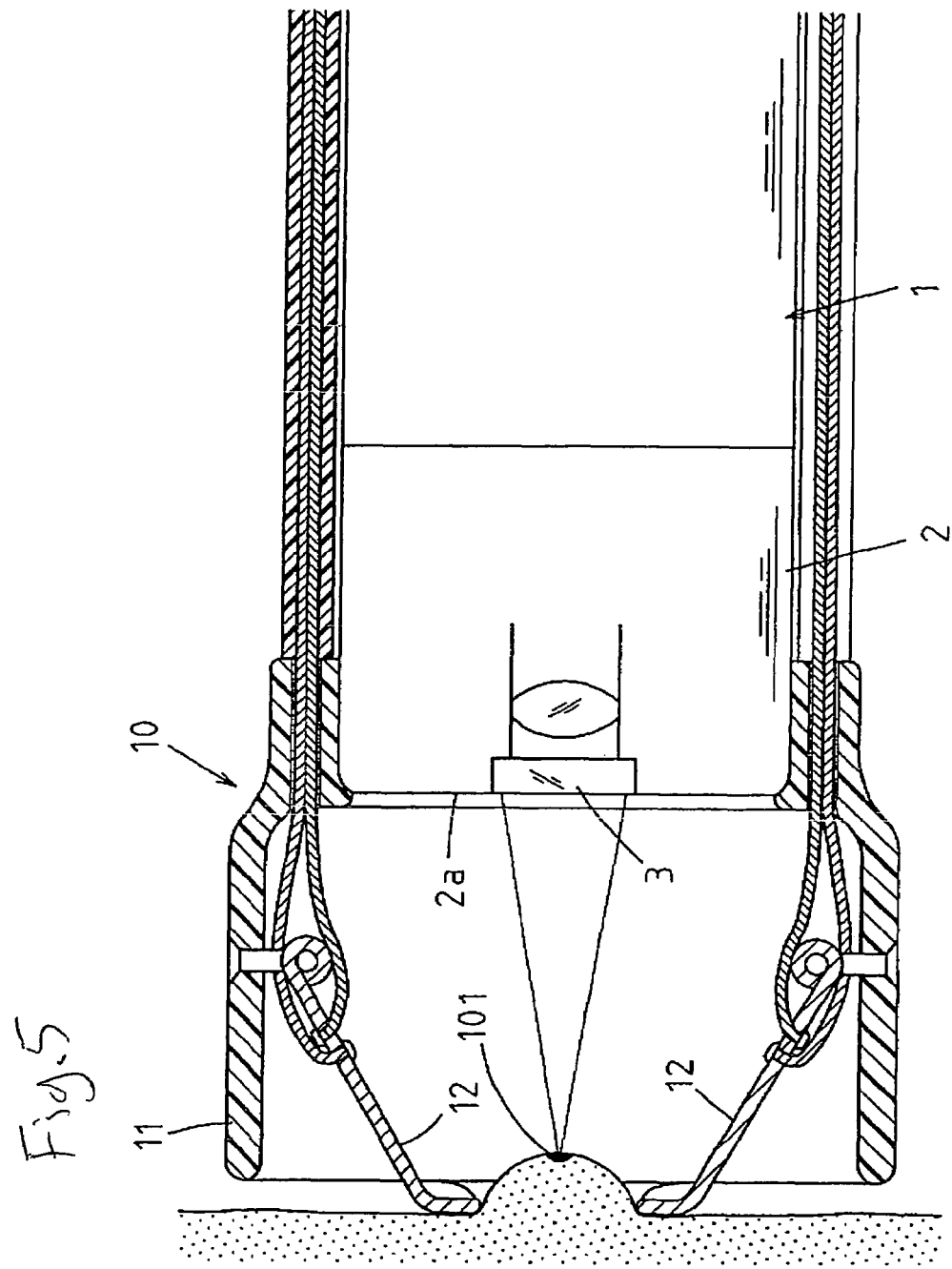

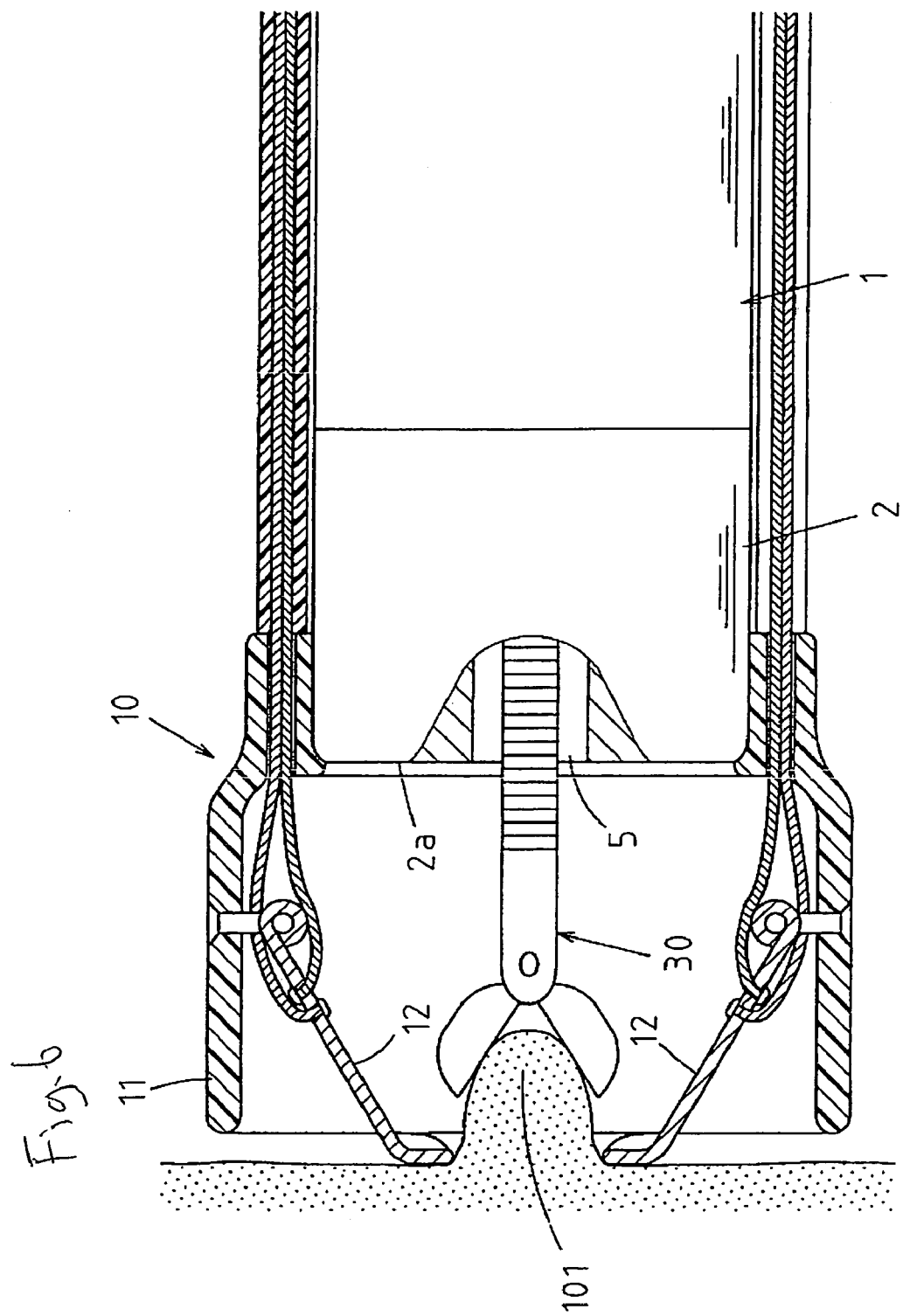

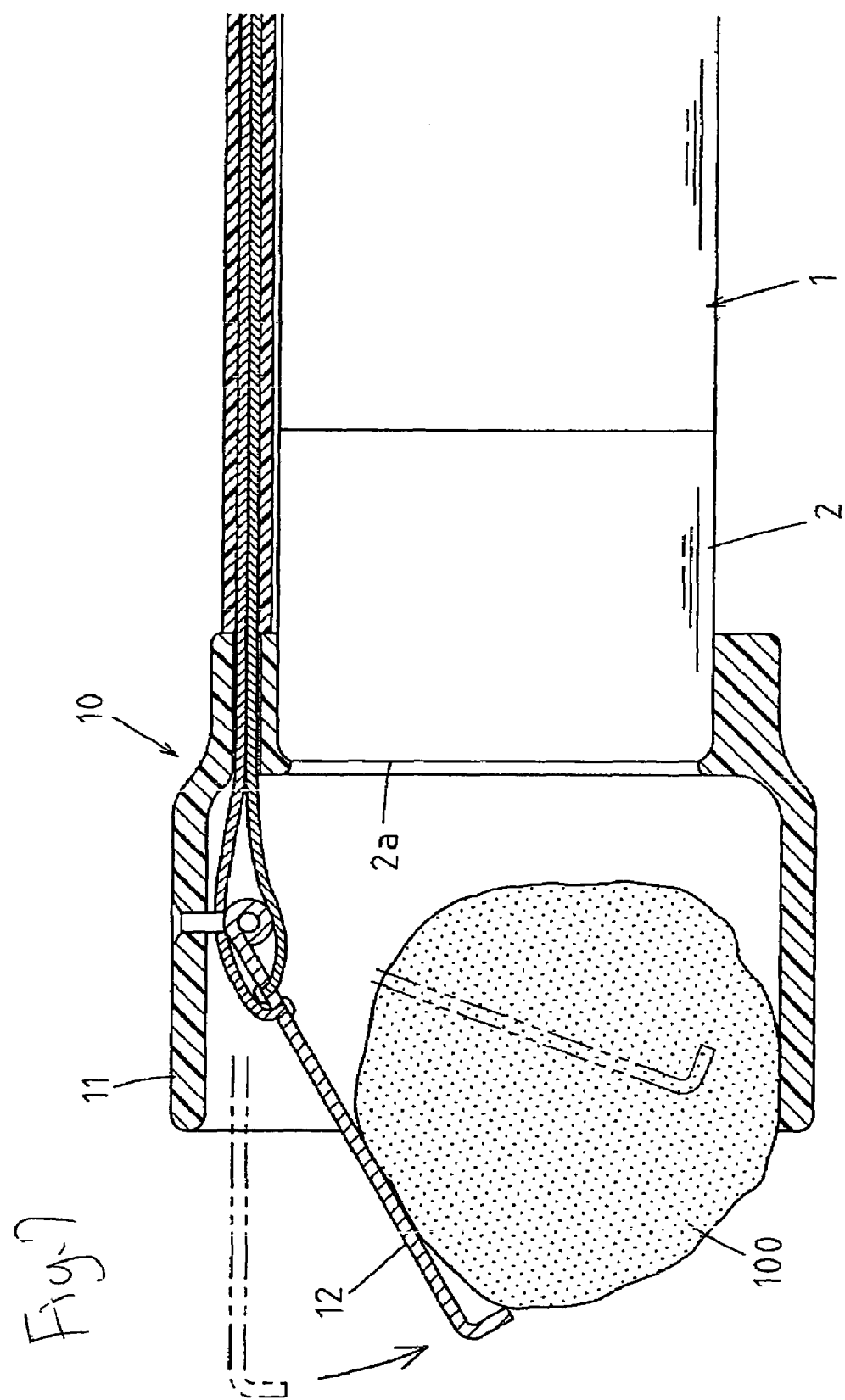

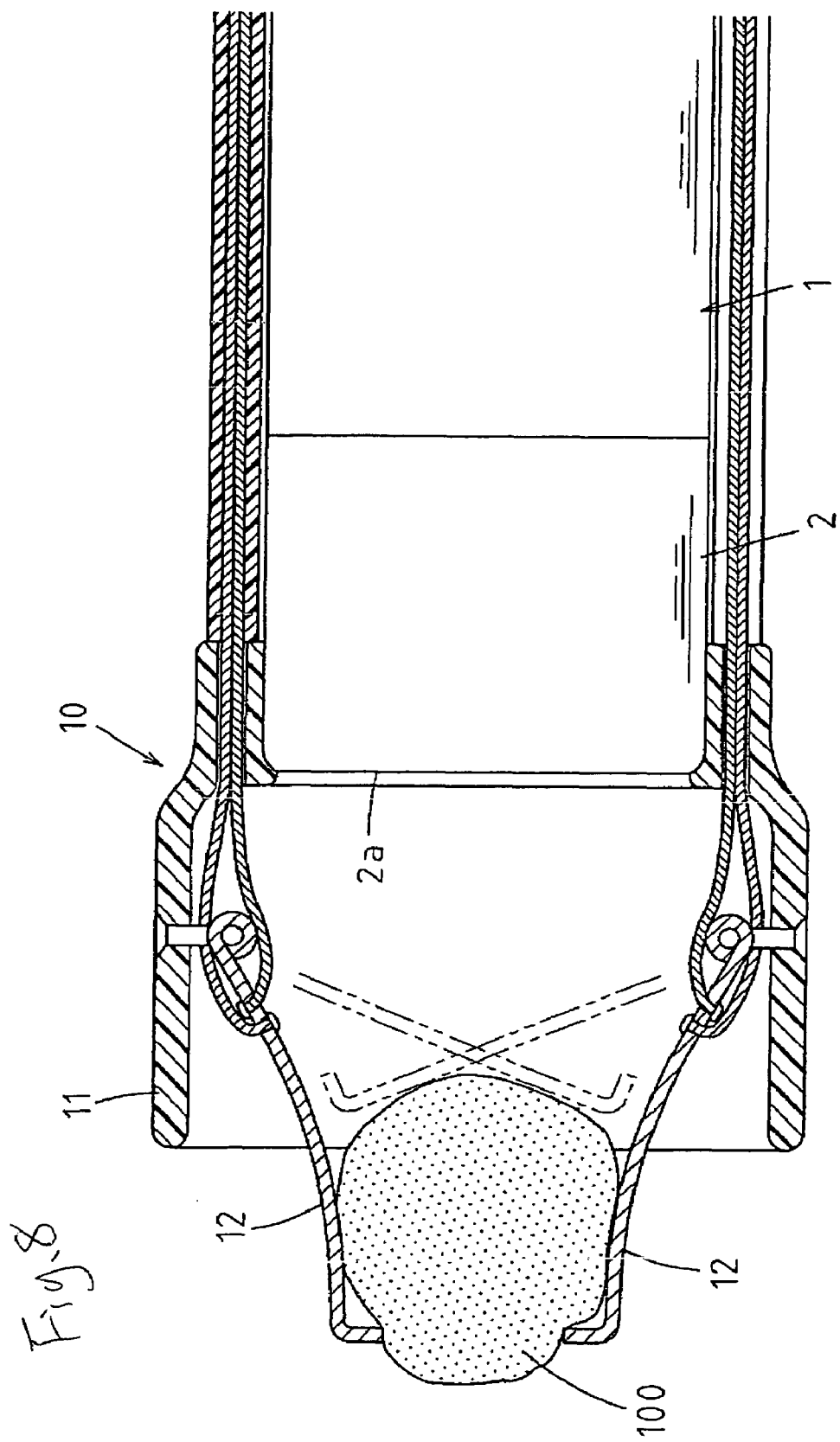

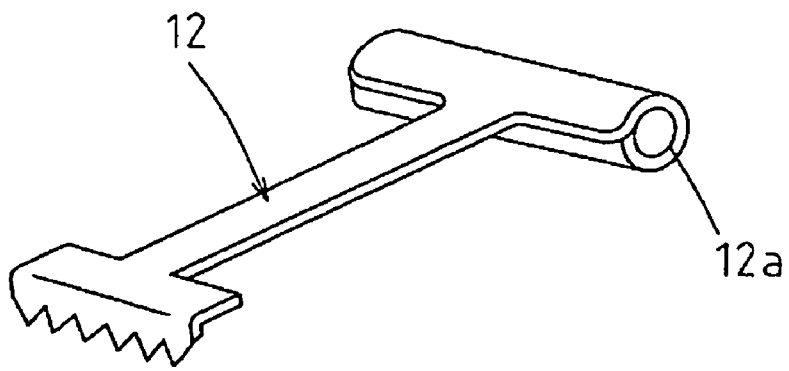
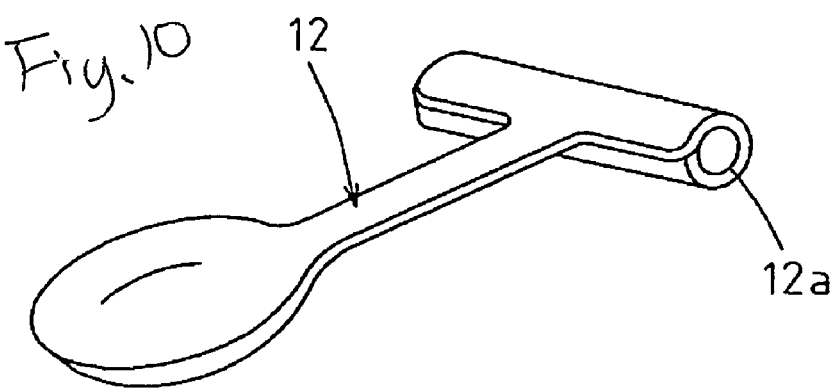
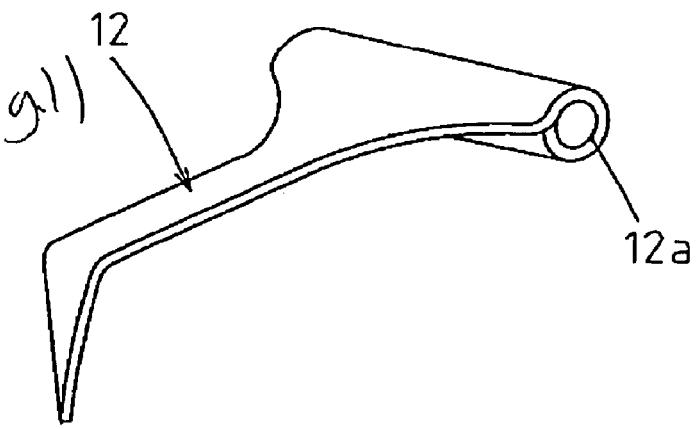

)
TREATMENT INSTRUMENT FOR ENDOSCOPE

BACKGROUND OF THE INVENTION

The present invention relates to a treatment instrument for an endoscope.

Generally, according to a treatment instrument for an endoscope, an operating wire is arranged to insert into a flexible sheath inserted and detached into and from a treatment instrument inserting channel of the endoscope, and treatment pieces arranged at a front end portion of the flexible sheath are made to be able to open and close from a side of the hand by an operating wire (for example, Patent References 1 to 5).

Patent Reference 1: JP-UM-63-151111
Patent Reference 2: JP-A-8-38496
Patent Reference 3: JP-A-3-295551
Patent Reference 4: JP-UM-A-5-9503
Patent Reference 5: JP-A-7-8450

However, in order to insert and detach the treatment pieces into and from the treatment instrument inserting channel of the endoscope, an outer diameter of the treatment pieces needs to be smaller than an inner diameter of the treatment instrument inserting channel and therefore, only a small-scaled treatment can be carried out in the background art.

SUMMARY OF THE INVENTION

Hence, it is an object of the invention to provide a grabbing instrument for an endoscope capable of easily and safely carrying out a large-scaled treatment without being influenced by a boldness of a treatment instrument inserting channel of the endoscope used.

In order to solve the aforesaid object, the invention is characterized by having the following arrangement.

(1) A treatment instrument for an endoscope, comprising:
  a front end hood that is provided to a distal end of an inserting portion of the endoscope;
  a supporting member that is provided inside the front end hood;
  a treatment member that is rotatably supported by the supporting member; and
  an operating wire that is coupled to the treatment member and extended rearwardly from the front end hood,
  wherein the treatment member is rotated about the supporting member by operating to extract and retract the operating wire at a base side of the endoscope.

(2) The treatment instrument according to (1), wherein the treatment member includes a grabbing member, the grabbing member is rotatably supported by the supporting member at a rear side of the grabbing member,
  the grabbing member is rotated about the supporting member at a vicinity of an opening of the front end food by operating to extract and retract the operating wire at a base side of the endoscope.

(3) The treatment instrument according to (2), wherein the supporting member extends in a peripheral direction of the front end food.

(4) The treatment instrument according to (2), wherein a plurality of the grabbing members are arranged substantially at equal intervals around an axis line of the front end hood.

(5) The treatment instrument according to (2), wherein the grabbing member is contained in the front end hood when the grabbing member is in a closed state, and a portion proximate to front ends of the grabbing member is projected from a front end of the front end hood when the grabbing member is in an opened state.

(6) The treatment instrument according to (2), wherein the grabbing member is provided with a spring performance and is elastically flexed by grabbing a foreign matter.

(7) The treatment instrument according to (2), wherein a high frequency current is made to be able to conduct to the grabbing member.

(8) The treatment instrument according to (1), wherein
  the treatment member includes a pair of beak-shaped treatment members,
  the operating wires are coupled to rear sides of the pair of beak-shaped treatment members, respectively,
  the pair of beak-shaped treatment members are rotatably supported by the supporting member, and
  the pair of beak-shaped treatment members are opened and closed like a beak at a vicinity of an opening of the front end food by operating to extract and retract the operating wires at the base side of the endoscope.

(9) The treatment instrument according to (8), wherein rotating axes of the pair of beak-shaped treatment members are coincided with each other.

(10) The treatment instrument according to (8), wherein the supporting member extends in a diameter direction of the front end food.

(11) The treatment instrument according to (10), wherein the supporting member is supported by the front end hood at opposite end portions of the supporting member.

(12) The treatment instrument according to (10), wherein the supporting member is projected from a side wall portion of the front end hood.

(13) The treatment instrument according to (8), wherein the pair of beak-shaped treatment members are bipolar high frequency electrodes, and an electrically insulating member supported by the treatment member supporting member is arranged between the pair of beak-shaped treatment members.

(14) The treatment instrument according to (8), wherein the pair of beak-shaped treatment members are one of biopsy forceps, grabbing forceps, scissors and monopolar high frequency electrodes.

(15) The treatment instrument according to (8), wherein a portion proximate to front ends of the pair of beak-shaped treatment members is projected from the opening of the front end hood to a front side.

(16) The treatment instrument according to (8), wherein the front end hood is formed with a notch for eliminating interference of the opened pair of beak-shaped treatment members with the front end hood.

(17) The treatment instrument according to (1), wherein two of the operating wires are coupled to the treatment member,
  when one of the operating wires is operated, the treatment member is opened, and
  when the other operating wire is operated, the treatment member is closed.

(18) The treatment instrument according to (1), wherein an operating wire guide tube through which the operating wire is passed is provided at a vicinity of an outer edge of a rear end of the front end hood.

(19) The treatment instrument according to (1), wherein the front end hood is made of transparent material.

BRIEF DESCRIPTION OF THE DRAWINGS

FIG. 5 is a sectional view of a side face in a second state of using the grabbing instrument for an endoscope according to the first embodiment of the invention.

FIG. 6 is a sectional view of a side face in a third state of using the grabbing instrument for an endoscope according to the first embodiment of the invention.

FIG. 7 is a sectional view of a side face in a state of using a grabbing member of a grabbing instrument for an endoscope according to a second embodiment of the invention.

FIG. 8 is a sectional view of a side face of a state of using a grabbing member of a grabbing instrument for an endoscope according a third embodiment of the invention.

FIG. 9 is a perspective view of a grabbing member of a grabbing instrument for an endoscope according to a fourth embodiment of the invention.

FIG. 10 is a perspective view of a grabbing member of a grabbing instrument for an endoscope according to a fifth embodiment of the invention.

FIG. 11 is a perspective view of a grabbing member of a grabbing instrument for an endoscope according to a sixth embodiment of the invention.

DETAILED DESCRIPTION OF PREFERRED EMBODIMENTS

An embodiment of the invention will be explained in reference to the drawings.

First Embodiment

Figure 1:
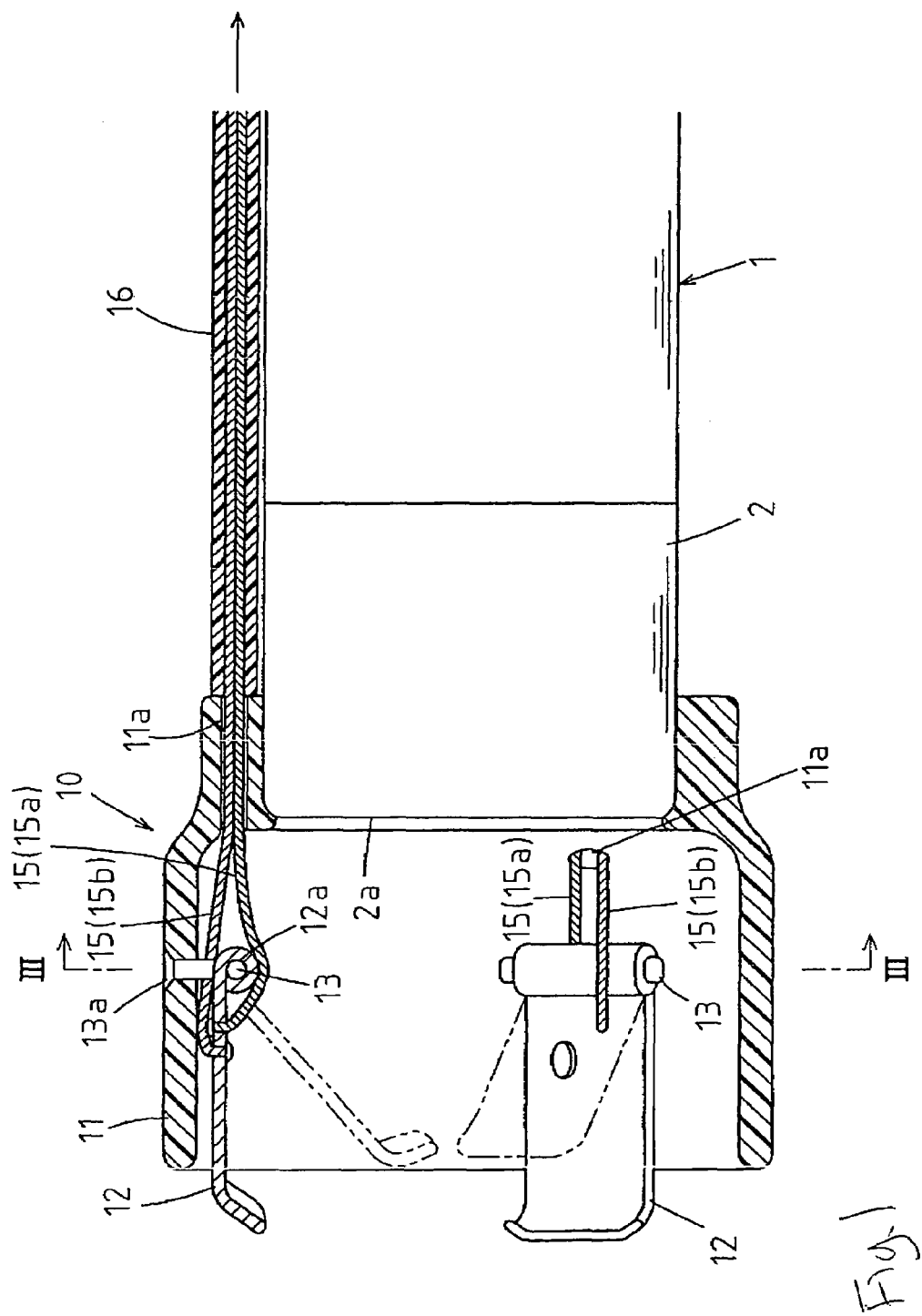
FIG. 1 is a sectional view of a side face in a state of attaching a grabbing instrument for an endoscope according to a first embodiment of the invention to the endoscope.
Figure 2:
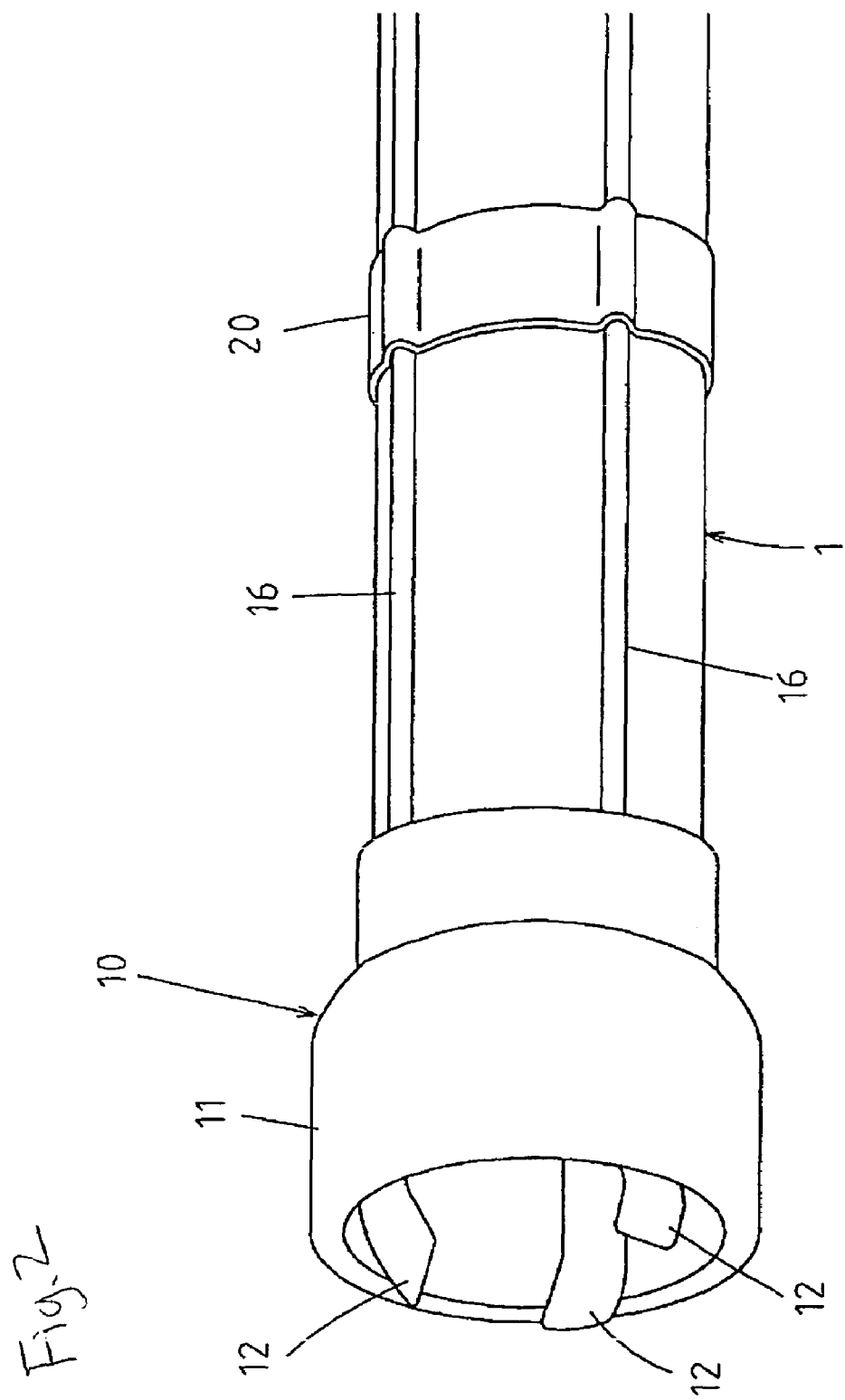
FIG. 2 is an outlook view in the state of attaching the grabbing instrument for an endoscope according to the first embodiment of the invention to the endoscope.

FIG. 1 is a sectional view of a side face in a state in which a grabbing instrument 10 which corresponds to a treatment instrument is attached to a front end portion main body 2 constituting a distal end portion of an endoscope inserting portion 1 made of a flexible tube. FIG. 2 is an outlook view, and FIG. 3 is a sectional view taken along a line III-III of FIG. 1.

A rear half portion of a front end hood 11 provided at the grabbing instrument 10 is formed in a shape of a cylinder having a diameter nearly the same as that of a front end portion of the front end portion main body 2, is formed of a plastic material having an elasticity or the like and can be tightly fitted to fix to the front end portion main body 2 from a front end side thereof by being deformed elastically and can also be detached therefrom. Incidentally, the rear half portion and the front end portion main body 2 may be provided with a groove and a projection which are engaged with each other.

Figure 3:
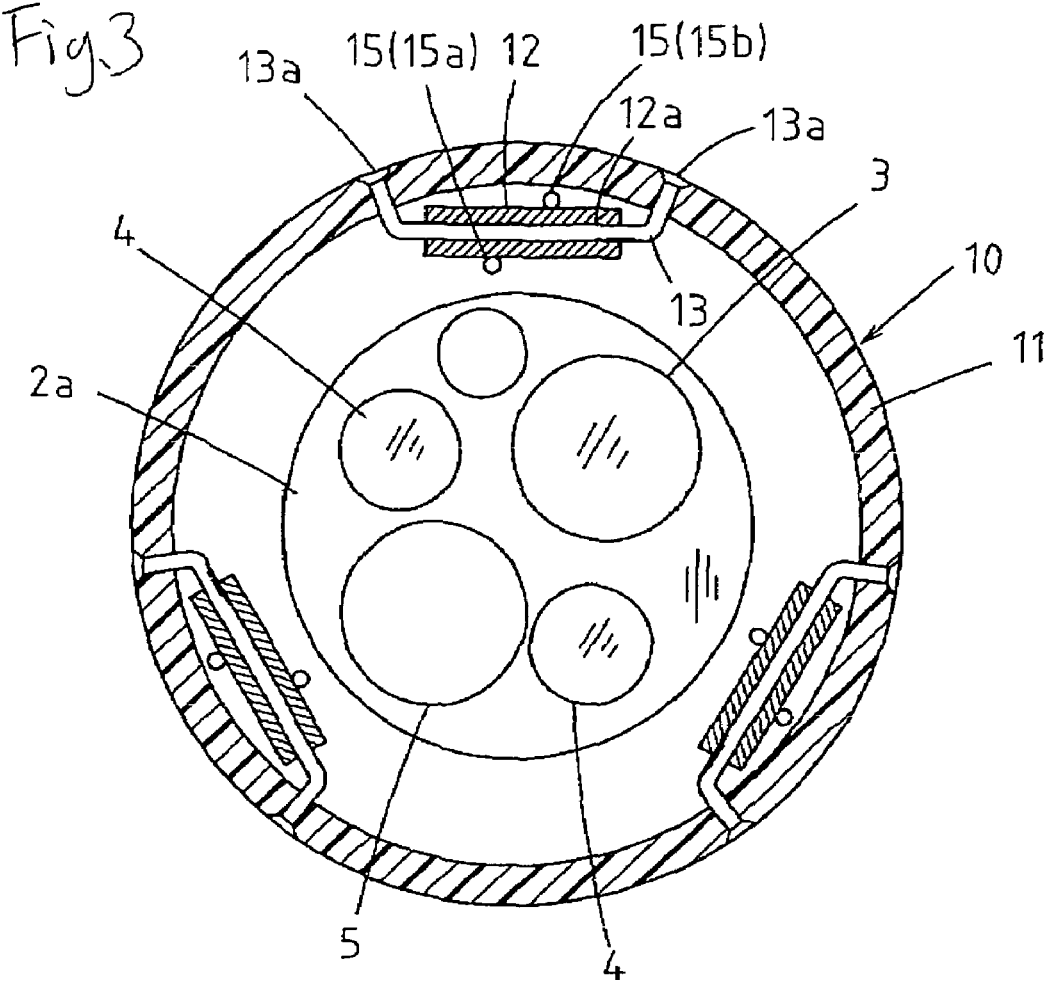
FIG. 3 is a sectional view of taken along a line III-III of FIG. 1 of the grabbing instrument for an endoscope according to the first embodiment of the invention.

As shown by FIG. 3, an observing window 3, an illuminating window 4 and a treatment instrument projecting port 5 are arranged at a front end face 2a of the front end portion main body 2, and the front end hood 11 is attached to the front end portion main body 2 such that the front end hood 11 does not obstruct front sides thereof.

At a vicinity of an inner peripheral face at inside of the front end hood 11 is arranged a grabbing member 12 (treatment member) for grabbing a foreign matter or the like so as to direct in a longitudinal direction in a state that a front end portion thereof is projected to a front side from a front end of the front end hood 11, and a supporting shaft 13 is loosely inserted and fitted into a shaft hole 12a formed at a rear end portion of the grabbing member 12.

The supporting shaft 13 is straightly arranged in a peripheral direction at a position proximate to an inner peripheral face of the front end hood 11, and two end portions 13a thereof are fixedly attached to the front end hood 11 as shown in FIG. 3. Any means of bonding, welding or the like may be used for the fixing the supporting shaft.

When the grabbing member 12 is in an opened state shown by bold lines in FIG. 1, the grabbing member 12 is directed straightly in the longitudinal direction and a portion thereof proximate to a front side thereof is projected to a front side from the front end of the front end hood 11, and the grabbing member 12 is disposed in a state of being substantially extended along the inner peripheral face of the front end hood 11. Therefore, the grabbing member 12 hardly obstacles an observing field of view directed from the observing window 3 to the front side. The wire may be made of any string such as silk, yarn and the like.

The grabbing section 12 is connected with respective distal end portions of a pair of operating wires 15 at a position frontward from the shaft hole 12a. The pair of operating wires 15 pass through a wire passing hole 11a formed to penetrate the rear half portion of the front end hood 11 in a direction in parallel with an axis line thereof and are arranged to insert loosely into a guide tube 16 extended rearward therefrom over an entire length of the guide tube 16.

The guide tube 16 is arranged along an outer face of the endoscope inserting portion 1 and is fastened to fix to the endoscope inserting portion 2 by a removable fastening strap 20 or the like (may be an adhering tape or the like), and a base side (side of the hand) thereof, not illustrated, is connected with an operating portion for operating to extract and retract the operating wire 15.

Owing to such a constitution, when a closing direction operating wire 15a is operated to pull from the side of the hand, as shown by two-dotted chain lines in FIG. 1, the grabbing member 12 is pivoted in a direction of a center axis of the front end hood 11 about the supporting shaft 13 to be brought into a closed state in which the grabbing member 12 is contained inside the front end hood 11 and when an opening direction operating wire 15b is operated to pull from the side of the hand, the grabbing member 12 is brought back to the opened state shown by bold lines.

According to the embodiment, three of the grabbing members 12 are arranged around the axis line of the front end hood 11 at intervals of 120° and the three grabbing members 12 are simultaneously operated to open and close by operating to extract and retract the operating wires 15 connected to the respective grabbing members 12 simultaneously from the side of the operating portion.

According to the grabbing instrument of the endoscope constituted in this way, when the grabbing instrument is guided into the body along with the endoscope inserting portion 1, the grabbing member 12 is brought into the opened state to observe the front side by the endoscope and when the grabbing instrument passes the stricture portion, inside of the sphincter muscle or the like, the grabbing member 12 is brought into the closed state to prevent the grabbing section 12 from impairing the mucous membrane.

Figure 4:
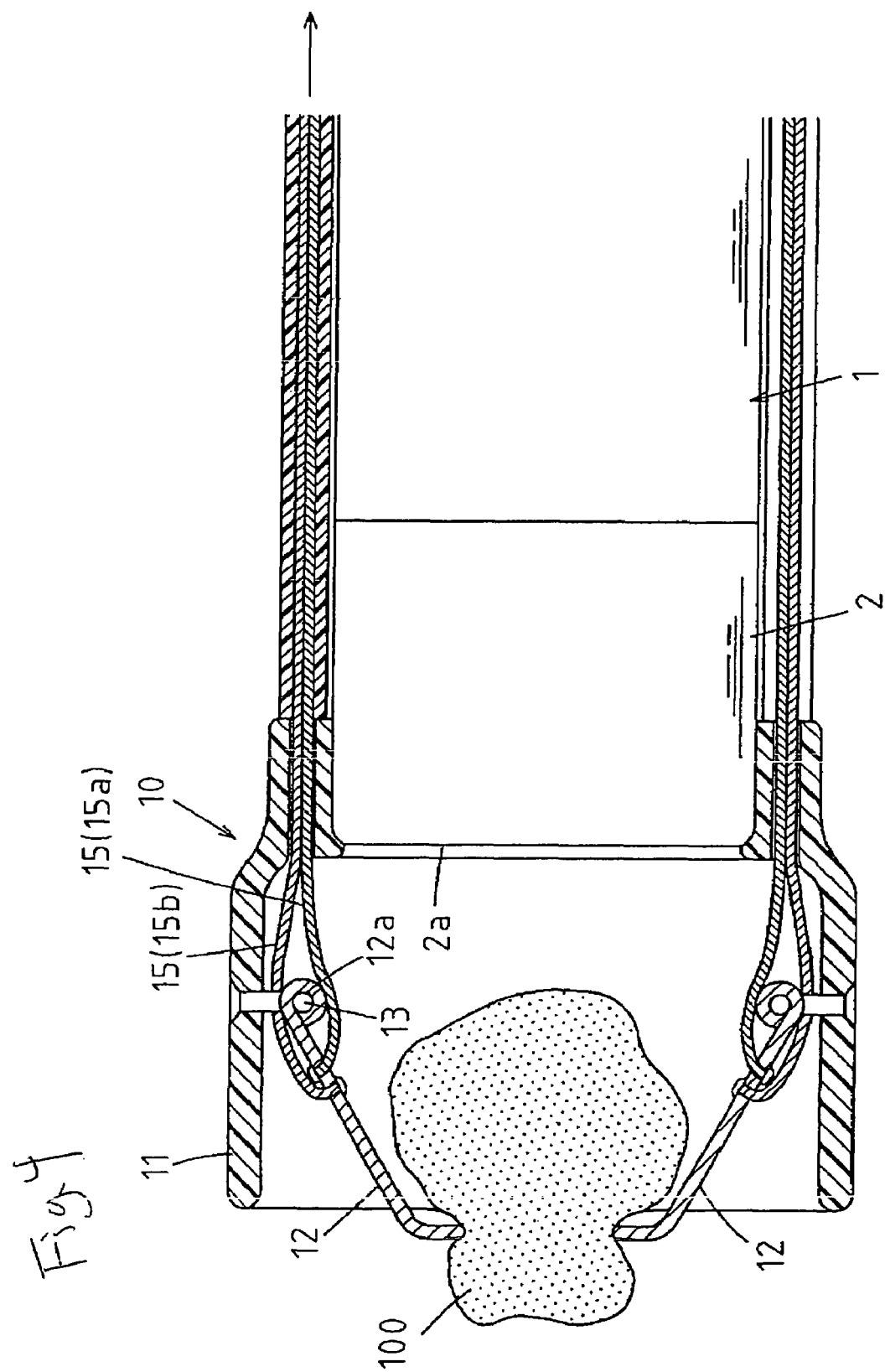
FIG. 4 is a sectional view of a side face in a state of using the grabbing instrument for an endoscope according to the first embodiment of the invention.

When the grabbing instrument encounters a foreign matter constituting a grabbing target, as shown by FIG. 4, a foreign matter 100 can be grabbed to recover by directing the grabbing member 12 to the foreign matter 100 to operate from the opened state to the closed state, and the foreign matter 100 having a size of substantially a diameter of the front end hood 11 can easily be recovered. Further, a section including the two grabbing members 12 is illustrated.

In the case inside of the observing window 3 includes a zoom optical system or the like for enlarged observation, microscopic enlarged observation can easily be carried out by pressing an affected portion 101 by the grabbing member 12 to fix it.

When incision of the mucous membrane or the like is carried out as shown by FIG. 6, by pressing the affected portion 101 by the grabbing member 12 to fix it, incision of the mucous membrane can safely be carried out by forceps 30 or the like projected from the treatment instrument projecting port 5 and injection or the like can safely be carried out similarly.

Second and Third Embodiments

The invention is not limited to the above-described embodiment but, for example, as shown by second and third embodiments shown by FIG. 7 and FIG. 8, there may be provided only one of the grabbing member 12 or two thereof at interval of 180°, or four or more thereof may be arranged.

In the case of a single one of the grabbing member 12 as shown by FIG. 7, the grabbing member 12 can be formed to prolong considerably, and the prolonged grabbing member 12 can completely be contained in the front end hood 11 when the prolonged grabbing member 12 is brought into the closed state. In the case of two of the grabbing members 12 as shown by FIG. 8, by arranging the two grabbing members 12 to intersect with each other, the grabbing members 12 can be formed to be prolonged considerably, the grabbing members 12 can completely be contained in the front end hood 11.

When the grabbing member 12 is formed by a material having spring performance, as shown by FIG. 8, the foreign matter 100 having a brittleness or the like can be grabbed to recover without destructing the foreign matter 100 by elastically flexing the grabbing members 12 when grabbing the foreign matter 100.

Fourth to Ninth Embodiments

Figure 12:
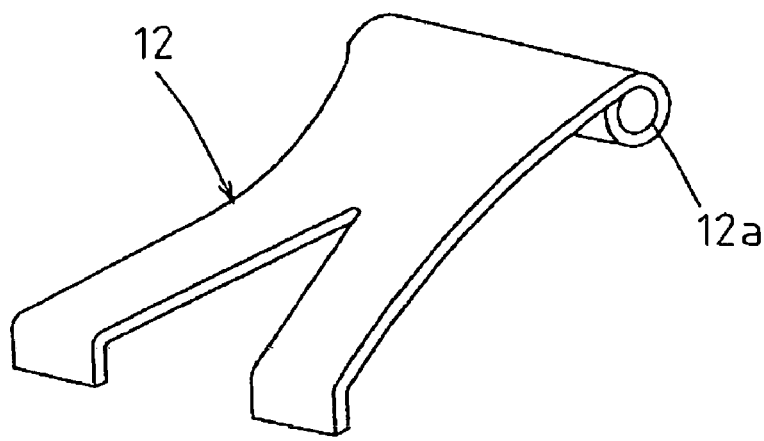
FIG. 12 is a perspective view of a grabbing member of a grabbing instrument for an endoscope according to a seventh embodiment of the invention.
Figure 13:
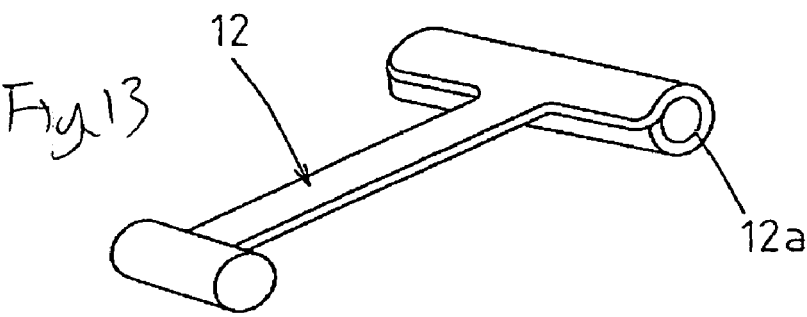
FIG. 13 is a perspective view of a grabbing member of a grabbing instrument for an endoscope according to an eighth embodiment of the invention.

A variety of shapes of the grabbing member 12 may be provided in accordance with a grabbing object or the like such as, for example, a rake shape as shown by FIG. 9, a spoon shape as shown by FIG. 10, a crane beak shape as shown by FIG. 11, a bifurcated shape as shown by FIG. 12, a shape attached with a soft rubber rod at a front end thereof as shown by FIG. 13 and so on.

Figure 14:
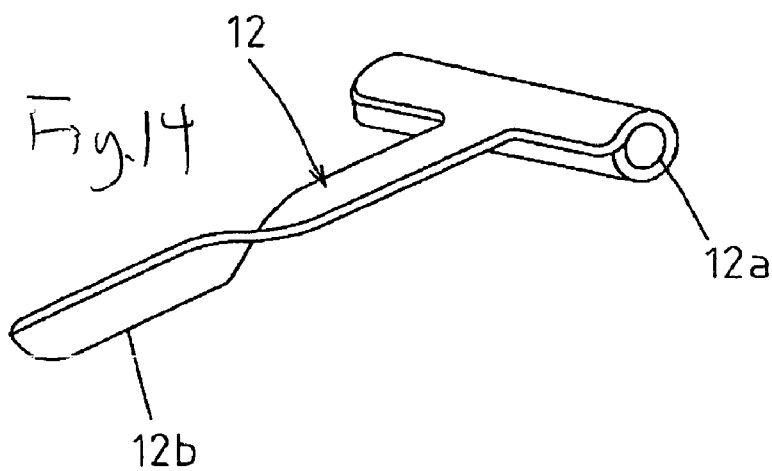
FIG. 14 is a perspective view of a grabbing member of a grabbing instrument for an endoscope according to a ninth embodiment of the invention.

When a portion 12b proximate to a front side of the grabbing member 12 is formed in a shape of a knife as shown by FIG. 14, the grabbed foreign matter 100 can be cut by exerting a large closing force thereto, further, when the grabbing member 12 is constituted to be able to conduct a high frequency current, hemostasis can also be carried out while cutting the foreign matter 100.

Tenth Embodiment

Figure 19:
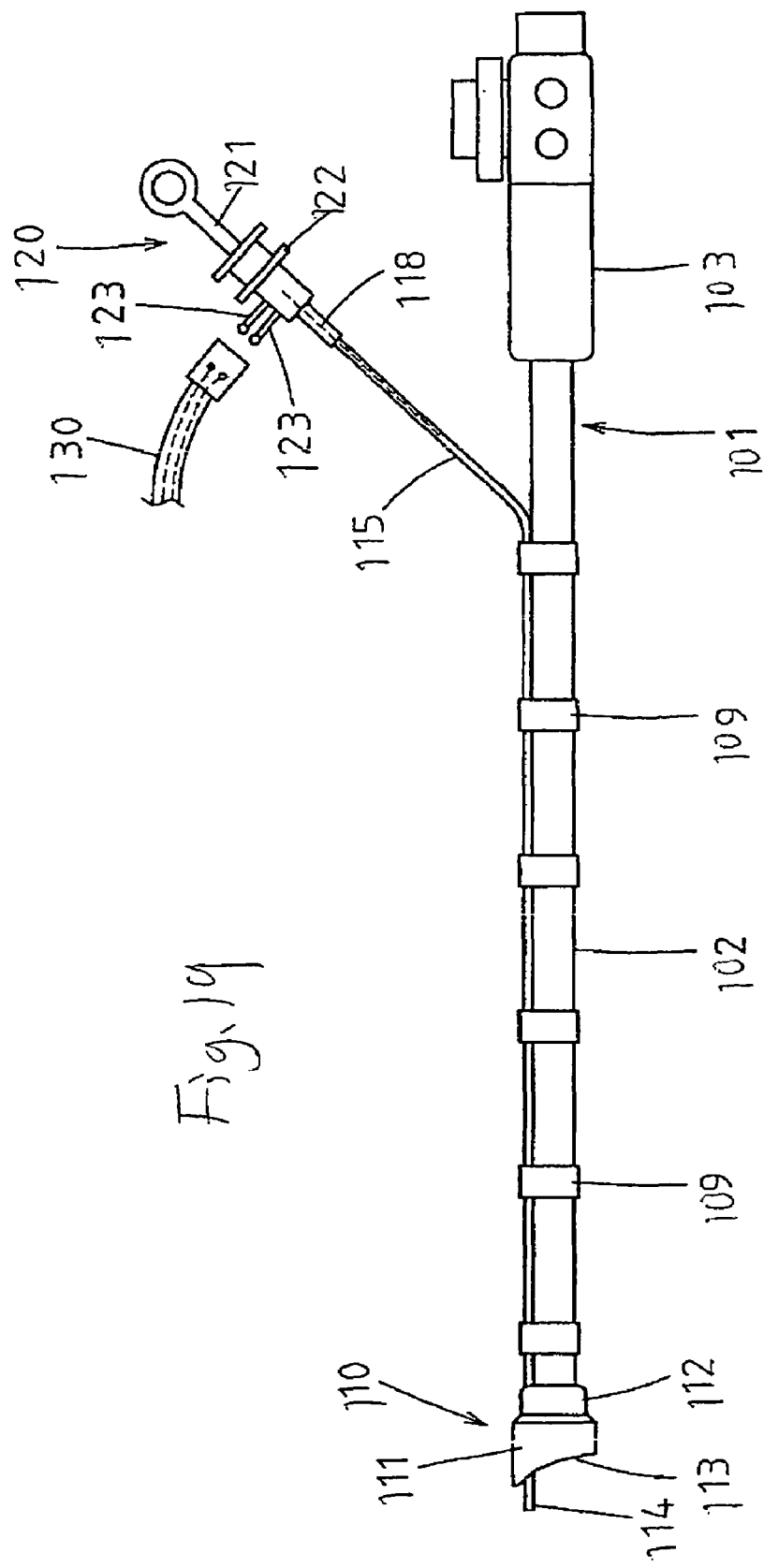
FIG. 19 is a side view showing a total constitution in the state in which the beak type treatment instrument for the endoscope according to the tenth embodiment of the invention is attached to the endoscope.

FIG. 19 shows a state of attaching a beak type treatment instrument 110 to an endoscope 101, reference numeral 102 designates an endoscope inserting portion in a shape of a flexible tube, and reference numeral 103 designates an endoscope operating portion connected to a base end of the endoscope inserting portion 2.

A rear half portion of a front end hood 111 provided at the beak type treatment instrument 110 constitutes a cylindrical attaching and detaching portion 112 attachable and detachable to and from a front end portion of the endoscope inserting portion 102 by being elastically deformed, and a front side portion of a beak-shaped treatment member 114 arranged at inside of the front end hood 111 is projected frontward from a front end opening portion 113 of the front end hood 111.

An operating wire guide tube 115 extended rearward from the cylindrical attaching and detaching portion 112 of the front end hood 111 is arranged to a base side of the endoscope inserting portion 112 along an outer face of the endoscope inserting portion 102 and is fastened to fix to the endoscope inserting portion 102 by detachable fastening straps 109 at a plurality of portions thereof in the midway.

A base end of the operating wire guide tube 115 is connected with an operating portion 120. By operating to slide a sliding operating piece 122 relative to an operating portion main body 121, an operating wire 118 inserted into the operating wire guide tube 115 over an entire length thereof is extracted and retracted in an axial line direction to thereby enable to open and close the beak-shaped treatment members 114 in the beak-shaped shape.

The operating portion 120 is projected with two connection terminals 23 for two positive and negative poles for connecting a high frequency power source cord 130. Therefore, a high frequency treatment of a bipolar (two poles) type can be carried out by connecting two pieces of the operating wires 18 to a positive pole and a negative pole of a high frequency power source, not illustrated, independently from each other, as necessary.

A high frequency treatment of a monopolar (single pole) type can also be carried out by utilizing the connecting terminal 123 for the positive pole in the two connecting terminals 123, and in the case of carrying out a mechanical treatment without using a high frequency current, the connection terminals 123 may not be utilized.

Figure 15:
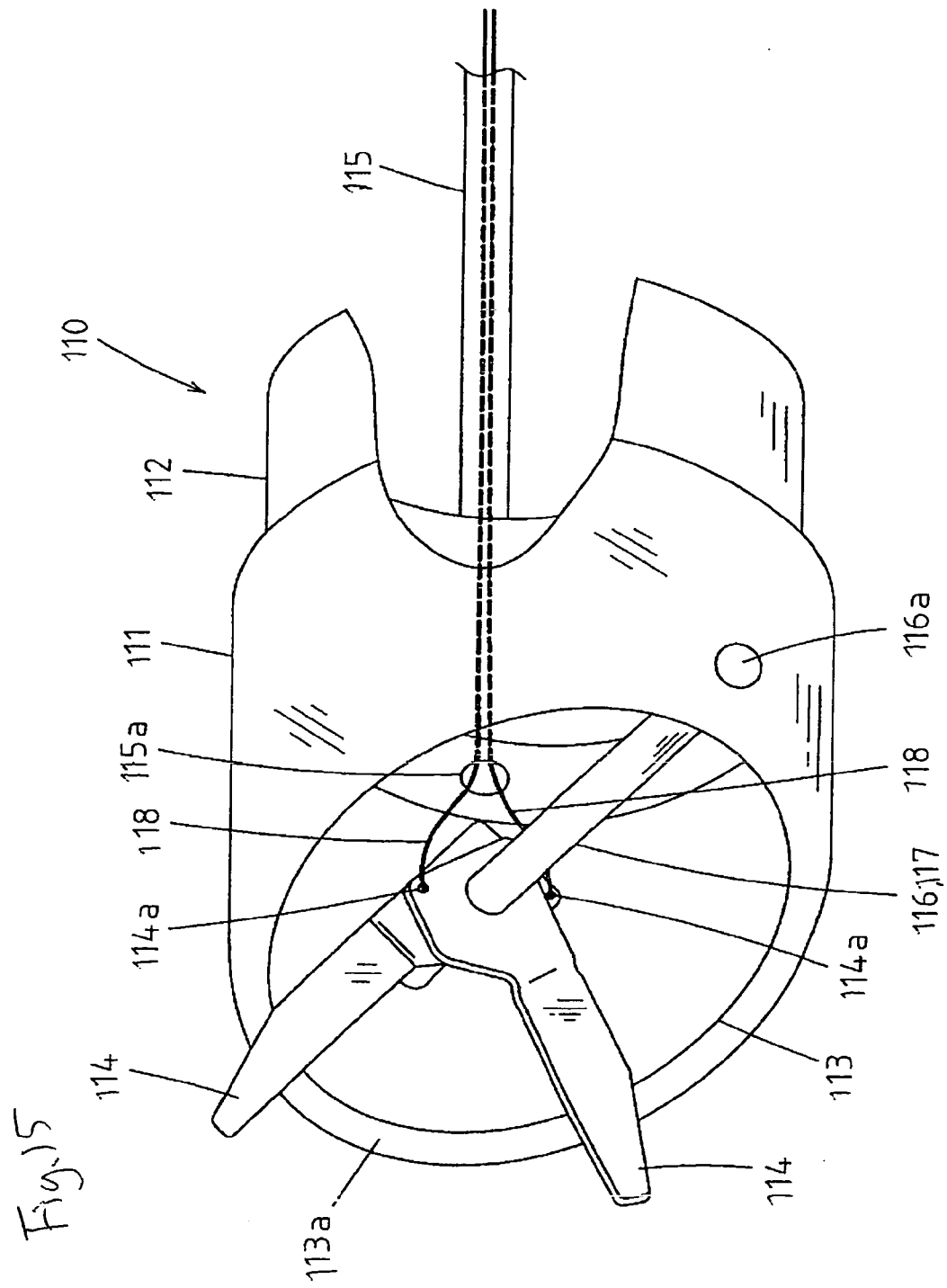
FIG. 15 is a perspective view showing to cut to remove a portion of a state of opening beak-shaped treatment members in a state in which a beak type treatment instrument for an endoscope according to a tenth embodiment of the invention is not attached to the endoscope.
Figure 16:
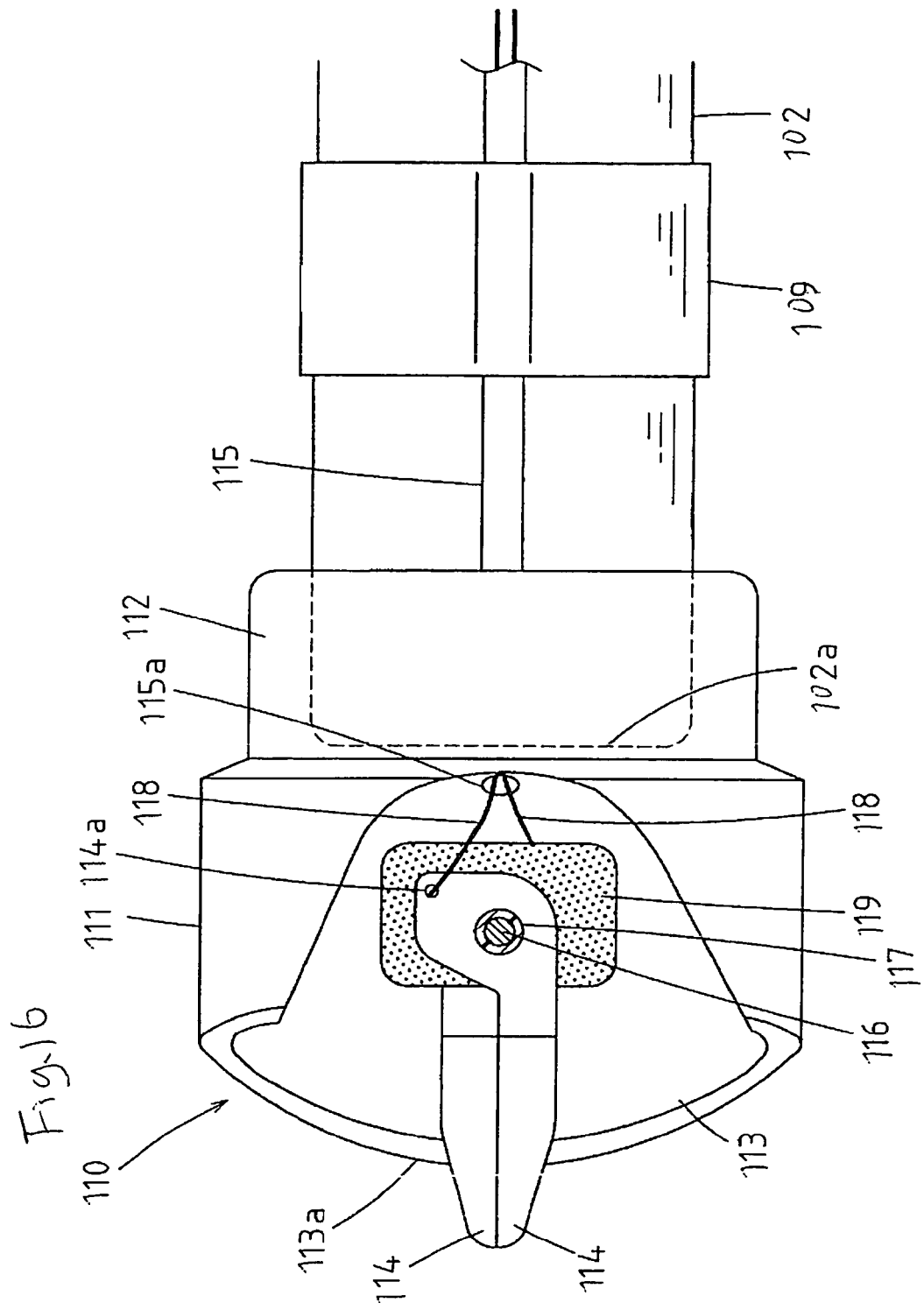
FIG. 16 is a sectional view of a side face portion in a state of closing the beak-shaped treatment members in a state in which the beak type treatment instrument of the endoscope according to the tenth embodiment of the invention is attached to the endoscope.
Figure 17:
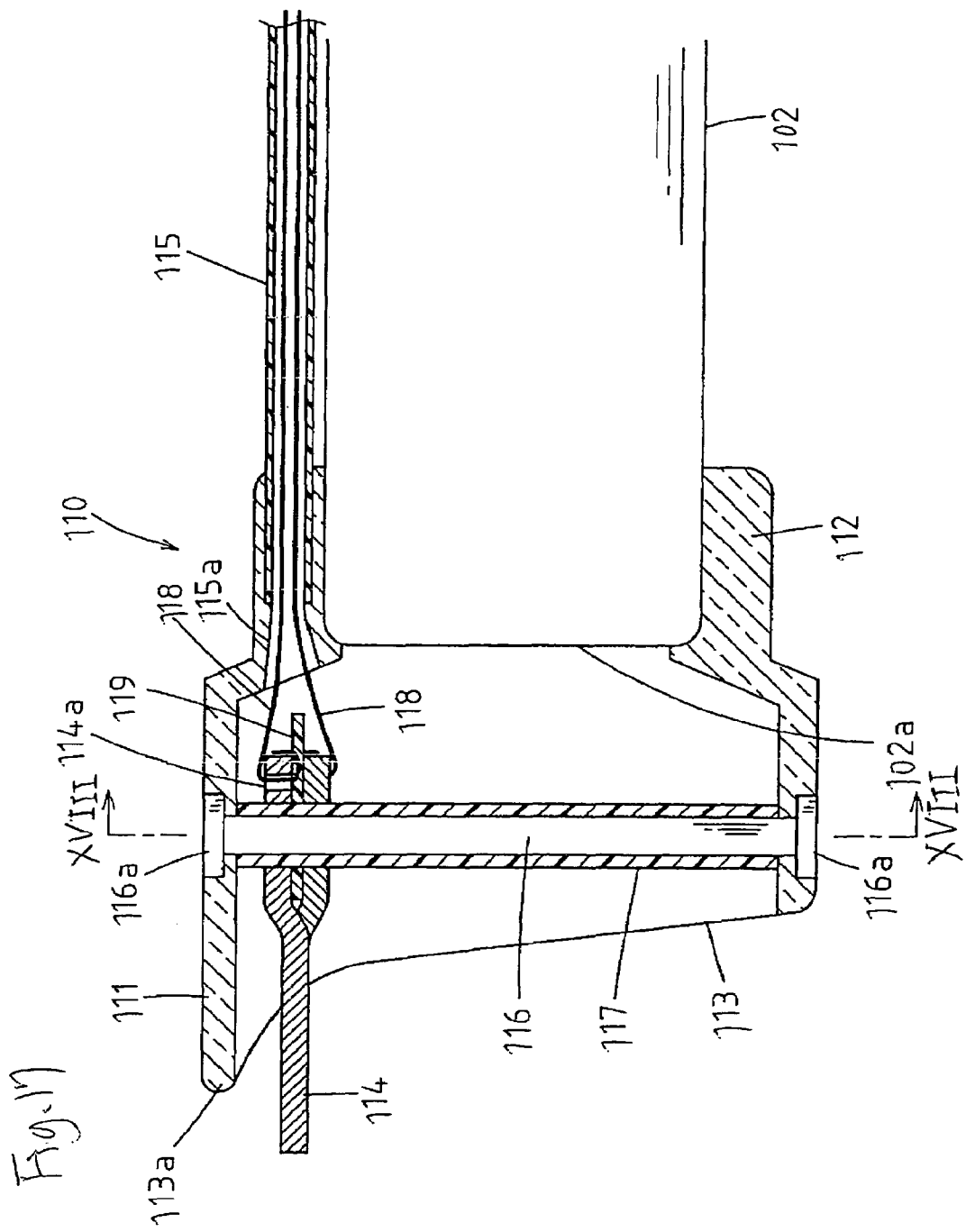
FIG. 17 is a sectional view of a plane in the state in which the beak type treatment instrument for the endoscope according to the tenth embodiment of the invention is attached to the endoscope.
Figure 18:
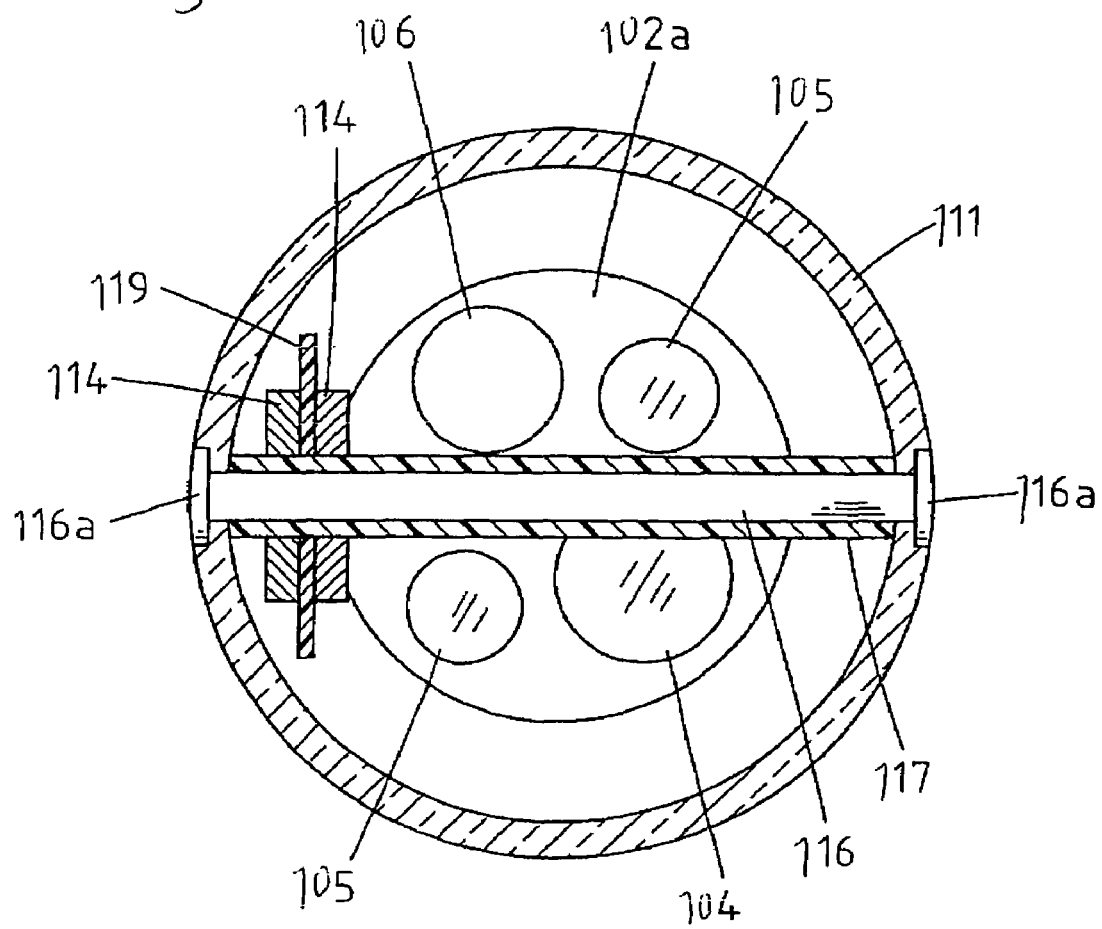
FIG. 18 is a sectional view (front sectional view) taken along a line XVIII-XVIII of FIG. 17 in the state in which the beak type treatment instrument for the endoscope according to the tenth embodiment of the invention is attached to the endoscope.

FIG. 15 is a perspective view of a state in which a front end portion of the beak-shaped treatment instrument 110 is not attached to the front end portion of the endoscope inserting portion 102 (however, the state is illustrated by cutting to remove a portion thereof), FIG. 16 is a sectional view of a side face portion in a state in which the front end portion of the beak-shaped treatment instrument 110 is attached to the front end portion of the endoscope inserting portion 102, FIG. 17 is a sectional view of a plane thereof, and FIG. 18 is a sectional view taken along a line XVIII-XVIII of FIG. 17.

The front end hood 111 of the beak type treatment instrument 110 is formed in a cylindrical shape bolder than a diameter of the front end portion of the endoscope inserting portion 102 by a transparent plastic material, and the cylindrical attaching and detaching portion 112 constituting the rear half portion is tightly fitted to the front end portion of the endoscope inserting portion 102. However, the front end portion of the endoscope inserting portion 102 and the cylindrical attaching and detaching portion 112 may be with a groove and a projection which are engaged with each other to fix it.

An observing window 104, an illuminating window 105 and a suction port 6 or the like are arranged at front end face 102a of the endoscope inserting portion 102, and the front end opening portion 113 is formed over an entire face of a front end portion of the front end hood 111 such that the front end hood 111 does not obstruct front sides thereof. The front end hood 111 of the embodiment is formed with a projected end 113a at which a portion thereof proximate to the beak-shaped treatment members 114 is projected to a front side to be longer than other portion.

A treatment member supporting member 115 in a shape of a round bar for turnably supporting the pair of beak-shaped treatment members 114 in the beak-shaped shape is arranged inside the front end hood 111 in a state of crossing the front end hood in a diameter direction. Opposite end portions 116a of the treatment member supporting member 116 are respectively fixed to a side wall of the front end hood 111. Although the fixing is carried out by mechanical clamping, the fixing may be carried out by any means of screwing to adhere, welding or the like.

The treatment member supporting member 116 may be arranged to deviate from a center of the front end hood 111 to a pertinent position displaced in a radial direction to avoid overlapping with a front side of an effective pupil diameter of the observing window 104 such that the treatment member supporting member 116 does not significantly obstructs an observing field of view by the observing window 104.

According to the embodiment, the treatment member supporting member 116 is covered with an electrically insulative insulating pipe 117 of, for example, an ethylene tetrafluoride resin tube or the like. However, the insulating pipe 117 can be omitted when the beak-shaped treatment members 114 carry out only a mechanical treatment.

The pair of beak-shaped treatment members 114 are formed in a shape of scissors according to the embodiment, and respectively formed with a hole formed at a position functioning as a rotational fulcrum, through which the treatment member supporting member 116 (and the insulating pipe 117) are inserted without rattle but to a degree of not restricting freedom of rotation.

An insulating spacer 119 made of an insulative is arranged between the pair of beak-shaped treatment members 114, and is provided with a small frictional resistance of, for example, an ethylene tetrafluoride resin sheet or the like by being interposed therebetween.

The insulating spacer 119 is supported by the treatment member supporting member 116 by passing the treatment member supporting member 116 through a hole bored there. However, illustration of the insulating spacer 119 is omitted in FIG. 15 and the insulating spacer 119 can be omitted when the beak-shaped treatment members 114 are not high frequency electrodes of a bipolar type.

A wire passing hole 115a for passing the pair of operating wires 118 is formed through inside of a wall of the cylindrical attaching and detaching portion 112. A front end portion of the operating wire guide tube 115 is inserted thereto from a rear side to be fixed to bond. Front end portions of the pair of operating wires 118 are led out from the wire passing hole 115a to the front side and respectively connected to engaging holes 114a formed at vicinities of rear ends of the beak-shaped treatment members 114.

Therefore, by operating to extract and retract the operating wires 118 in the axial line direction from the side of the operating portion 120 connected to the base end of the operating wire guide tube 115, the pair of beak-shaped treatment members 114 are operated to be opened and closed like the beak-shaped shape about the treatment member supporting member 116. Further, FIG. 15 shows a state of opening the beak-shaped treatment members 114 and FIG. 16 shows a state of closing the beak-shaped treatment members 114.

The pair of operating wires 118 are respectively coated with electrically insulative skin films such that the pair of operating wires 118 are not electrically conducted to each other. However, the electrically insulating skin film may be coated only on one of the operating wires 118. When the beak-shaped treatment members 114 carry out only a mechanical treatment, the electrically insulative skin film is not needed.

In use, the beak-shaped treatment instrument 110 constituted in this way is attached to the front end portion of the endoscope inserting portion 102 as shown by respective drawings other than FIG. 15 and is inserted into the body. In that case, when a guide tube or the like is inserted in advance from an inlet portion at inside of the body to a depth to some degree and the endoscope inserting portion 102 is inserted into the guide tube, the beak-shaped treatment members 114 can easily be inserted without being caught by the body wall or the like.

In inserting the beak-shaped treatment instrument 110, a state of the mucous membrane in the body frontward from the front end hood 111 can be observed from the observing window 104 of the endoscope 101, further, since the front end hood 111 is transparent, a surrounding situation can widely be observed also by way of the front end hood 111.

A size of the beak-shaped treatment members 114 is only restricted by a size of the front end hood 111 containing the beak-shaped treatment members 114 and therefore, the beak-shaped treatment members 114 can be formed much larger than that of the background art, and a large-scaled treatment (sampling, grabbing, incision, ablation, hemostasis or the like) can be carried out at the portions proximate to front ends of the beak-shaped treatment members 114 projected forward from the front end opening portion 113 of the front end hood 111.

In such a case of the large-scaled treatment, the beak-shaped treatment members 114 may be exerted with a large force, the treatment member supporting member 116 for supporting the beak-shaped treatment members 114 is fixed to the front end hood 111 and is not fluctuated and therefore, the large-scaled treatment can easily and safely be carried out in a stable state.

Ninth Embodiment

Figure 20:
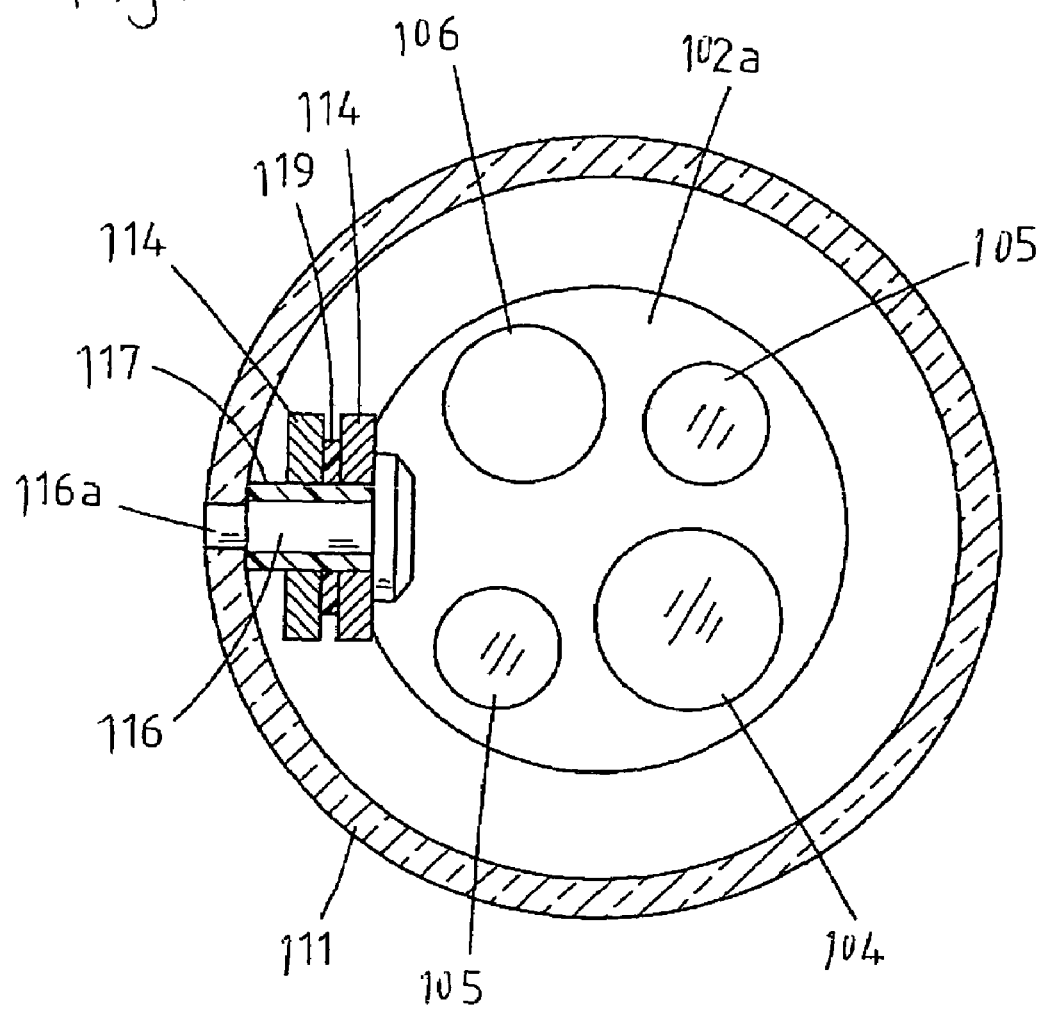
FIG. 20 is a front sectional view of a state in which a beak type treatment instrument for an endoscope according to a eleventh embodiment of the invention is attached to the endoscope.

The invention is not limited to the above-described embodiment but, for example, as shown by FIG. 20, the treatment member supporting member 16 may be constituted by a member in a pin-like shape by being arranged to project from a side wall portion of the front end hood 111 to an inner side in a state of a cantilever. By constituting in this way, front fields of view of the observing window 104 and the illuminating window can be made to be hampered hardly.

Twelfth Embodiment

Figure 21:
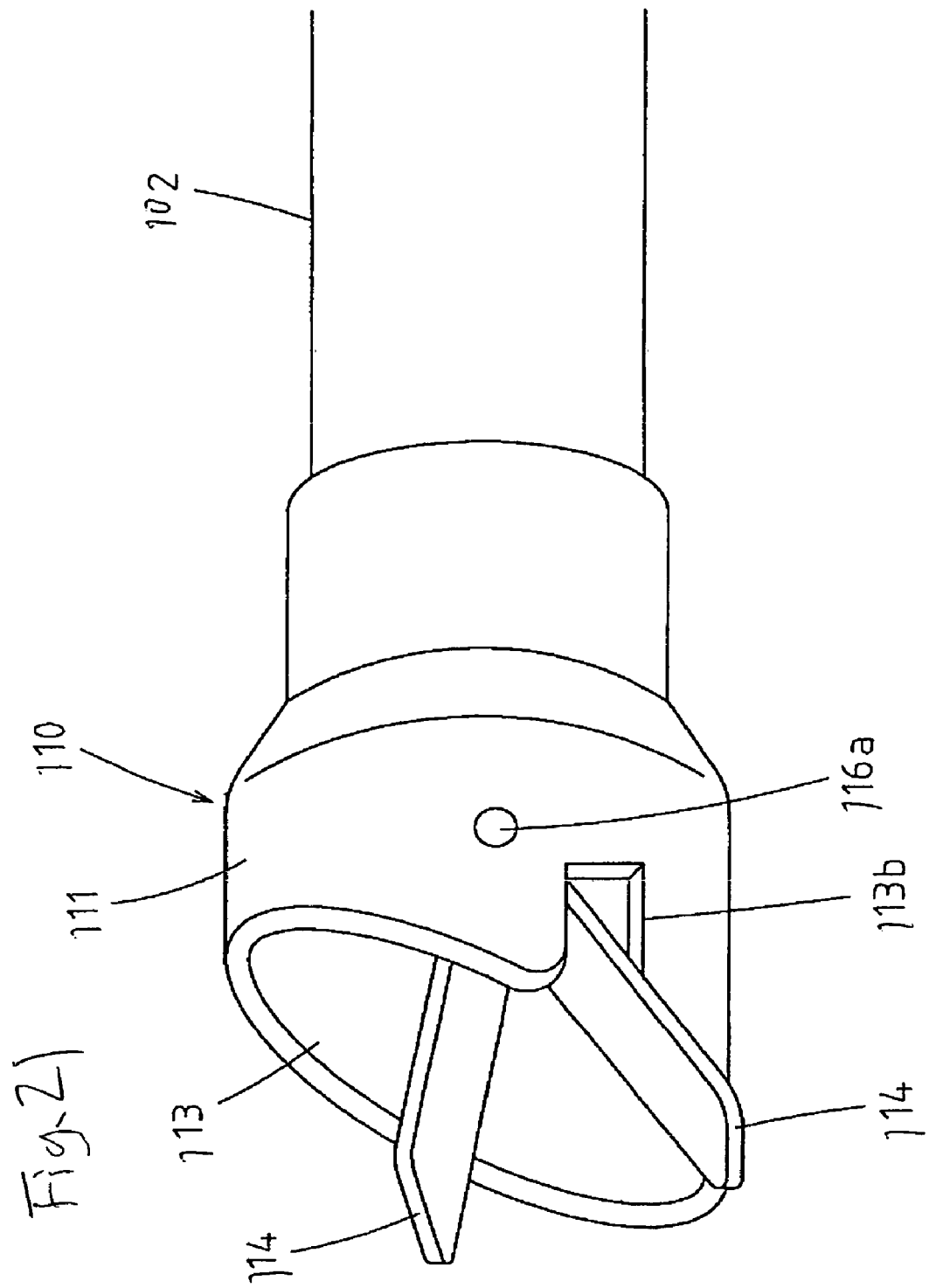
FIG. 21 is a perspective view of an outlook in a state in which a beak type treatment instrument for en endoscope according to a twelfth embodiment of the invention is attached to the endoscope.

As shown by FIG. 21, in the case in which the beak-shaped treatment members 114 are large grabbing members or the like, when notches 113b for eliminating interference with the front end hood 111 in opening the pair of beak-shaped treatment members 114 in the beak-shaped shape are formed continuously to a rear side from the front end opening portion 113, the beak-shaped treatment members 114 can be opened by a large amount.

Thirteenth Embodiment

Figure 22:
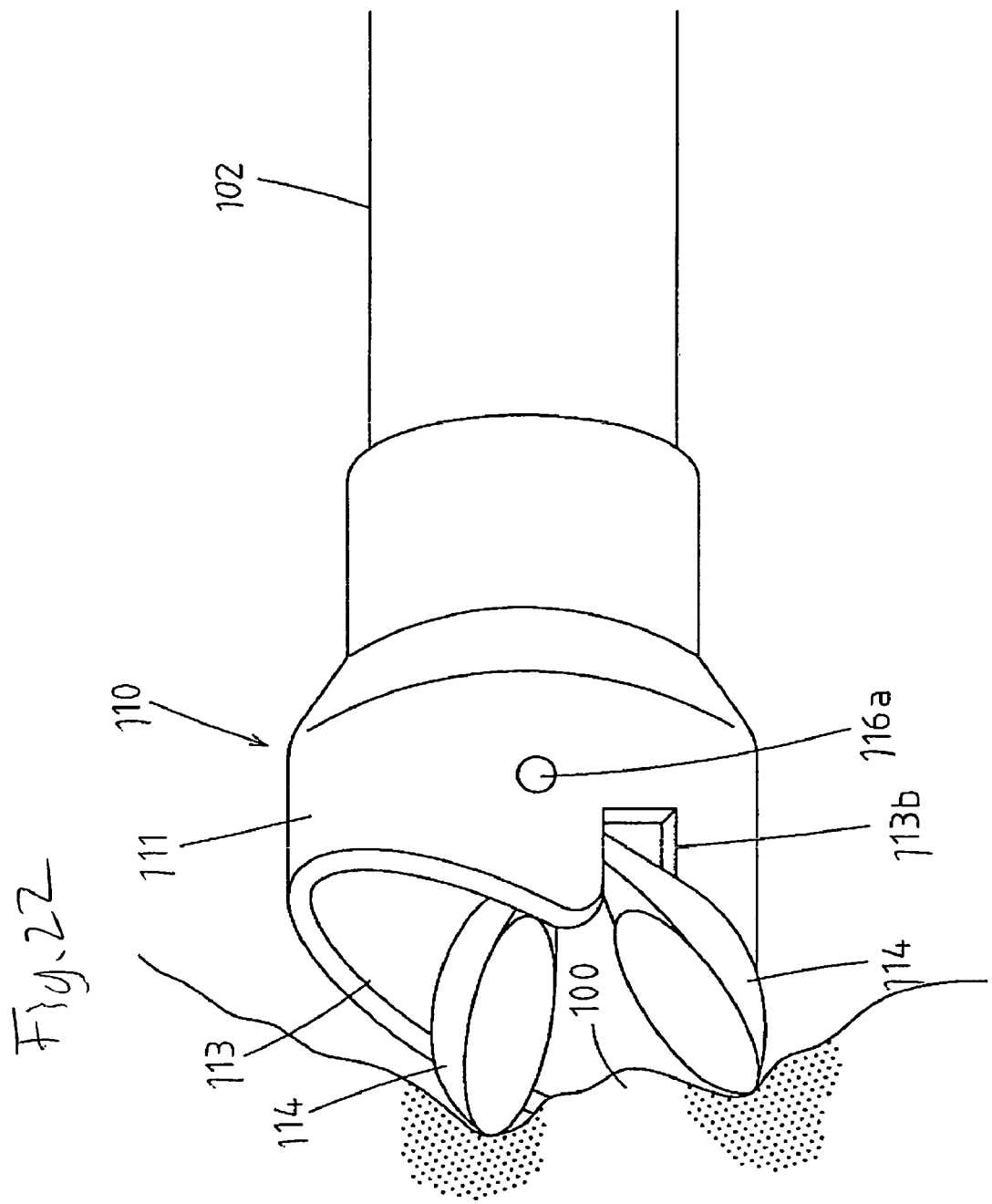
FIG. 22 is a perspective view of an outlook in a state in which a beak type treatment instrument for an endoscope according to a thirteenth embodiment of the invention is attached to the endoscope.

As shown by FIG. 22, in the case in which the beak-shaped treatment members 114 are hot biopsy forceps or the like, even when the beak-shaped treatment members 114 are not operated to open and close, a hemostasis treatment or the like can be carried out by only pressing the front ends of the beak-shaped treatment members 114 to the mucous membrane 100 of the affected part and conducting a high frequency current, conversely in sampling a tissue, even when the high frequency current is not conducted, a large tissue sample can be sampled by only opening and closing the beak-shaped treatment members 114.

What is claimed is:

1. A treatment instrument for an endoscope, comprising:
   a front end hood that is provided to a distal end of an inserting portion of the endoscope;
   a supporting member that is provided inside the front end hood;
   a treatment member that is rotatably supported by the supporting member, the treatment member including a grabbing member, the grabbing member being rotatably supported by the supporting member at a rear side of the grabbing member; and
   an operating wire that is coupled to the treatment member and extends rearwardly from the front end hood,
   wherein the grabbing member is rotated about the supporting member at a vicinity of an opening of the front end hood by the extension and retraction of the operating wire, at a base side of the endoscope;
   wherein the grabbing member is provided with a spring characteristic and is elastically flexed by grabbing a foreign matter.

2. The treatment instrument according to claim 1, wherein the supporting member extends in a peripheral direction of the front end hood.

3. The treatment instrument according to claim 1, wherein a plurality of the grabbing members are arranged substantially at equal intervals around an axis of the front end hood.

4. The treatment instrument according to claim 1, wherein the grabbing member is contained in the front end hood when the grabbing member is in a closed state, and
   a portion proximate to front ends of the grabbing member is projected from a front end of the front end hood when the grabbing member is in an opened state.

5. The treatment instrument according to claim 1, wherein a high frequency current is conductible to the grabbing member.

6. The treatment instrument according to claim 1, wherein two operating wires are coupled to the treatment member,
   when one of the operating wires is operated, the treatment member is opened, and
   when the other operating wire is operated, the treatment member is closed.

7. The treatment instrument according to claim 1, wherein an operating wire guide tube through which the operating wire extends, is provided at a vicinity of an outer edge of a rear end of the front end hood.

8. The treatment instrument according to claim 1, wherein the front end hood comprises transparent material.

9. A treatment instrument for an endoscope, comprising:
   a front end hood that is provided to a distal end of an inserting portion of the endoscope;
   a supporting member that is provided inside the front end hood;
   a treatment member that is rotatably supported by the supporting member, the treatment member including a pair of beak-shaped treatment members, the pair of beak-shaped treatment members being rotatably supported by the supporting member; and
   an operating wire that is coupled to the treatment member and extends rearwardly from the front end hood, the operating wire comprising operating wires that are coupled to rear sides of the pair of beak-shaped treatment members, respectively;
   wherein the pair of beak-shaped treatment members are opened and closed by rotation about the supporting member in a beak-like manner at a vicinity of an opening of the front end hood by the extension and retraction of the operating wires at the base side of the endoscope, and
   wherein the front end hood is configured with a notch for eliminating interference of the opened pair of beak-shaped treatment members with the front end hood.

10. The treatment instrument according to claim 9, wherein rotating axes of the pair of beak-shaped treatment members coincide with each other.

11. The treatment instrument according to claim 9, wherein the supporting member extends in a diameter direction of the front end hood.

12. The treatment instrument according to claim 11, wherein the supporting member is supported by the front end hood at opposite end portions of the supporting member.

13. The treatment instrument according to claim 11, wherein the supporting member is projected from a side wall portion of the front end hood.

14. The treatment instrument according to claim 9, wherein
the pair of beak-shaped treatment members are bipolar high frequency electrodes, and an electrically insulating member supported by the treatment member supporting member is arranged between the pair of beak-shaped treatment members.

15. The treatment instrument according to claim 9, wherein the pair of beak-shaped treatment members are one of biopsy forceps, grabbing forceps, scissors and monopolar high frequency electrodes.

16. The treatment instrument according to claim 9, wherein a portion proximate to front ends of the pair of beak-shaped treatment members is projected from the opening of the front end hood to a front side.

17. The treatment instrument for an endoscope according to claim 9, wherein an operating wire guide tube through which the operating wire extends, is provided at a vicinity of an outer edge of a rear end of the front end hood.

18. The treatment instrument for an endoscope according to claim 9, wherein the front end hood comprises transparent material.

* * * * *